(12) United States Patent
Hong

(10) Patent No.: US 11,529,128 B2
(45) Date of Patent: Dec. 20, 2022

(54) SPRING-LOADED DEVICE FOR ELICITING DEEP TENDON REFLEXES

(71) Applicant: University of South Florida, Tampa, FL (US)

(72) Inventor: Kevin Chao Hong, Temple Terrace, FL (US)

(73) Assignee: University of South Florida, Tampa, FL (US)

( * ) Notice: Subject to any disclaimer, the term of this patent is extended or adjusted under 35 U.S.C. 154(b) by 950 days.

(21) Appl. No.: 16/262,475

(22) Filed: Jan. 30, 2019

(65) Prior Publication Data

US 2019/0231251 A1 Aug. 1, 2019

Related U.S. Application Data

(60) Provisional application No. 62/623,830, filed on Jan. 30, 2018.

(51) Int. Cl.
| | |
|---|---|
| *A61B 9/00* | (2006.01) |
| *A61H 39/00* | (2006.01) |
| *A61B 5/00* | (2006.01) |
| *A61H 1/00* | (2006.01) |

(52) U.S. Cl.
CPC .............. *A61B 9/00* (2013.01); *A61B 5/4523* (2013.01); *A61H 39/00* (2013.01); *A61H 1/006* (2013.01); *A61H 1/008* (2013.01)

(58) Field of Classification Search
CPC ......... A61B 9/00; A61B 9/005; A61B 5/4523; A61B 5/4041; A61H 39/00; A61H 1/006; A61H 1/008; B25D 1/00; B25D 1/02; B25D 1/12; B25D 1/16; B25D 2250/371
See application file for complete search history.

(56) References Cited

U.S. PATENT DOCUMENTS

| | | | |
|---|---|---|---|
| 843,655 A | 2/1907 | Adell et al. | |
| 889,409 A | 6/1908 | Spalding | |
| 2,384,707 A | 9/1945 | Sweet | |
| 2,800,895 A | 7/1957 | Torricelli | |
| 3,543,603 A | 12/1970 | Gley | |
| 4,116,235 A * | 9/1978 | Fuhr | A61H 1/008 606/238 |

(Continued)

FOREIGN PATENT DOCUMENTS

WO 2017027954 A1 2/2017

*Primary Examiner* — David J. McCrosky
(74) *Attorney, Agent, or Firm* — Nicholas Pfeifer; Smith & Hopen, P. A.

(57) ABSTRACT

A deep tendon reflex-eliciting device actuated by pressure against a patient's skin, which releases a spring-loaded mass that delivers an impulse through a fully-enclosed housing. This device includes a weight contained within the casings, and a mainspring in communication with the weight. The mainspring has a bias toward expansion. In the compressed position, the mainspring is also compressed, and the weight is pushed backwards into the rear casing. The weight is released to be driven forward by the mainspring. The weight strikes the inside of the forward casing, delivering an impulse to a surface against Which the device is pressed. A reset spring can push apart the forward and rear casings to reset the device to its expanded position. A case screw is also included which is able to consistently set the impact force of the device.

16 Claims, 4 Drawing Sheets

(56) References Cited

U.S. PATENT DOCUMENTS

| | | | |
|---|---|---|---|
| 4,669,454 A * | 6/1987 | Shamos | A61H 1/008 173/120 |
| 6,370,993 B1 | 4/2002 | Pitstick | |
| 7,950,178 B1 | 5/2011 | Landies et al. | |
| 8,449,346 B2 | 5/2013 | Lee | |

* cited by examiner

SPRING-LOADED DEVICE FOR ELICITING DEEP TENDON REFLEXES

CROSS-REFERENCE TO RELATED APPLICATIONS

This nonprovisional application claims priority to U.S. Provisional Patent Application No. 62/623,830, entitled "Spring-Loaded Device for Eliciting Deep Tendon Reflexes," filed Jan. 30, 2018 by the same inventors, the entirety of which is incorporated herein by this reference.

TECHNICAL FIELD

This invention relates, generally, to neurological reflex testing. More specifically, it relates to medical devices and associated methodologies for testing deep tendon reflexes in patients or subjects. In addition, medical devices and associated methodologies for testing deep tendon reflexes in patients that are hypo-reflexive, normo-reflexive, and hyper-reflexive.

BACKGROUND

The physical exam is an important aspect of the physician-patient encounter. It is the first chance a doctor gets to contact and interact with the human body in order to identify if there is a possible abnormality with the patient. The physical exam has many parts, including a neurological assessment, which aims to identify pathology or injury of the central and peripheral nervous systems. The neurological exam is divided into multiple parts, the majority of which include examination of the corticospinal tracts by means of assessing motor activity of peripheral muscles, the spinothalamic tract by means of assessing sensory stimuli of pain and temperature, and of the dorsal columns and medial lemniscal tracts by means of assessing tactile information, proprioception, two-point discrimination and stereognosis. A neurology specialist, a neurologist, uses a reflex hammer to assess an individual's deep tendon reflexes (DTR), which are a component of the corticospinal tracts.

A reflex is a muscular contraction that is elicited as a response to a stimulus without conscious control. Deep tendon reflexes are muscle contractions which occur in response to stretching within tendons. They are normally present uniformly within all of a person's limbs. In neurology, reflexes are used to quickly determine the location of injury to the nervous system. To test/elicit deep tendon reflexes, a percussive reflex hammer is typically used, where a physician or other user/operator swings the hammer in an arc-like motion onto the tendon in question. However, this neurological reflex testing can be limited under certain circumstances when a strike upon the tendon is obstructed. For example, an adequate reflex hammer swing may be impeded if the patient has a condition, such as contractures, which limit the patient's range of motion to a tense, closed position, giving insufficient room to swing a reflex hammer, particularly to test the biceps reflex. Another example where a strike upon the tendon may be limited is in cases of severe obesity, where parts of the patient's upper arm may physically block a reflex hammer from contacting the tendon site. An example of a device that attempts to alleviate this issue is WO2017027954, though this disclosure presents additional drawbacks, such as the complexity of the mechanism.

There are many types of reflexes but of particular interest are the deep tendon reflexes, or myotatic reflexes, where the receptor neurons have relatively direct connections to the muscle spindle fibers. Normal DTRs result from the contraction of a muscle whose tendon has been stretched by an impulse elicited upon the tendon, for example, by a reflex hammer. Physicians are currently trained to subjectively grade the reflex responses at the bedside. These response levels are measured from 'O' to '4+', with '2+' being normal, and with 'O' designating no response at all. The presence of DTR responses less than 2+ may denote damage to the peripheral nervous system, more specifically the lower motor neuron. The presence of DTR responses greater than 2+ may suggest damage or pathology to the central nervous system, more specifically the upper motor neuron, or point to underlying anxiety or drug use. Asymmetry of reflexes (unequal reflex responses in the limbs), moreover, frequently implies central or peripheral nervous system perturbation. These findings are paramount in assessing multiple neurologically related medical illnesses and injuries, including hematomas of the brain, diabetic neuropathy, multiple sclerosis, tumours, genetic illnesses, not to mention innumerable and protean pathologic abnormalities. Despite the importance of this clinical window into the health of the nervous system, the current accepted technique of, and technology for, eliciting this physical sign, is over a century old. It relies on the subjective 'feel' and 'experience' of the examiner, which cannot be precisely calibrated on a repeatable basis, and is more 'eminence-based' than evidence-based.

Recent research has examined the force necessary to elicit a DTR at the knee, for example, as a quadricep reflex (see Marshall, G L, Little, J W. Deep tendon reflexes: a study of quantitative methods. J Spinal Cord Med (2002). 25: 94-99, incorporated by reference herein). Although this research was invaluable in quantifying DTRs, the metric used was not as robust as possible. The paper summarized that there was an unknown relationship between differing reflex hammers and the amount of force required to elicit a DTR.

Accordingly, what is needed is an improved apparatus for testing deep tendon reflexes in such difficult scenarios. However, in view of the art considered as a whole at the time the present invention was made, it was not obvious to those of ordinary skill in the field of this invention how the shortcomings of the prior art could be overcome.

While certain aspects of conventional technologies have been discussed to facilitate disclosure of the invention, applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

SUMMARY

This summary is provided to introduce a selection of concepts in a simplified form. These concepts are described in further detail in the detailed description of example embodiments of the disclosure below. This summary is not intended to identify key features or essential features of the claimed subject matter, nor is it intended to be used to limit the scope of the claimed subject matter.

Embodiments disclosed herein include structures to elicit deep tendon reflexes from a subject, as well as related methods for using the structures. For example, in accordance with one embodiment, a device for assessing reflexes in a subject, comprising: a forward casing; a rear casing coupled to the forward casing; wherein the forward and the rear casing form a housing; an activatable hammer within the housing, wherein the activatable hammer is capable of moving from a first ready position to a second activated position; an impulse generator operably connected to the activatable hammer, where the impulse generator provides an impulse to the activatable hammer to activate the hammer to the second activated position; a reset spring operably connected to the activatable hammer, wherein the reset spring facilitates return of the activatable hammer to the first ready position; a case screw operably connected to the impulse generator to provide control of the amount of force exerted by the impulse generator against the activatable hammer; wherein activation of the impulse generator activates the activatable hammer to exert force against the skin of a subject to elicit a reflex.

In additional embodiments, a device for assessing reflexes in a subject wherein the case screw comprises a stop at one end of the case screw to prevent the case screw from disengaging from the impulse generator, and where the case screw can be positioned by an end user to adjust the force exerted by the impulse generator against the activatable hammer.

In additional embodiments, a device for assessing reflexes in a subject wherein the stop is positioned to prevent the case screw from backing out of either side of the rear casing.

In additional embodiments, a device for assessing reflexes in a subject wherein the forward casing contains a sear that holds a weight toward the end of the rear casing in preparation for activation of the weight.

In additional embodiments, a device for assessing reflexes in a subject wherein when the sear is triggered by a ramp, the weight is released to be driven forward by the mainspring, the weight strikes the inside of the forward casing delivering an impulse to a surface against which the forward casing is pressed.

In additional embodiments, a device for assessing reflexes in a subject wherein the forward casing is coupled to the rear casing with an assembly tab which slides within an assembly channel.

In additional embodiments, a device for assessing reflexes in a subject wherein the housing further comprises a weight which slides within the housing under the force of the mainspring.

In additional embodiments, a device for assessing reflexes in a subject further comprising an elastomer head secured at the front end of the forward casing.

In additional embodiments, a device for assessing reflexes in a subject wherein the elastomer head may be composed of elastomers such as silicone or urethane rubber.

In additional embodiments, a device for assessing reflexes in a subject wherein the rear casing further comprises a ramp, an assembly tab, and a reset tab coupled to the rear casing by a spring guide which forms a hollow tube shape.

In additional embodiments, a device for assessing reflexes in a subject wherein the assembly tab, reset tab, and the ramp are symmetrically present on both sides of the rear casing.

In additional embodiments, a device for assessing reflexes in a subject wherein the case screw has markings to allow for setting the case screw at the same position with increased accuracy.

In further embodiments, a device for eliciting a deep tendon reflex in a subject, comprising: a forward casing; a rear casing coupled to the forward casing, wherein the forward and rear casings collectively are a housing; a weight enclosed within the housing; a mainspring having one end positioned at a rear surface of the rear casing and the opposite end positioned on the weight, where the mainspring has a bias of expansion; and a reset spring disposed through the weight and in communication with the rear casing and the front casing, wherein the device includes a resting position, a compressed position, and a released position, wherein the forward and rear casings are in slidable communication with each other between the expanded and compressed positions, wherein in the expanded position, the mainspring is unloaded, and the reset spring is unloaded, wherein in the compressed position, the mainspring is loaded, and the reset spring is loaded, wherein in the released position, the mainspring is unloaded, and the reset spring is loaded, such that during a transition between the compressed position and the released position, the weight travels forward within the housing and places a force on a from surface of the forward casing.

In further embodiments, A method of eliciting deep tendon reflex response from a subject, comprising: providing a reflex testing apparatus; wherein the reflex testing apparatus includes: a forward casing; a rear casing coupled to the forward casing; wherein the forward and the rear casing form a housing; an activatable hammer within the housing, wherein the activatable hammer is capable of moving from a first ready position to a second activated position; an impulse generator operably connected to the activatable hammer, where the impulse generator provides an impulse to the activatable hammer to activate the hammer to the second activated position; a reset spring operably connected to the activatable hammer, wherein the reset spring facilitates return of the activatable hammer to the first ready position; a case screw operably connected to the impulse generator to provide control of the amount of force exerted by the impulse generator against the activatable hammer; positioning the reflex testing apparatus against a subject's skin over a tendon; activating the reflex testing apparatus; wherein activation of the reflex testing apparatus elicits a deep tendon reflex in the subject.

In additional embodiments, a method for assessing reflexes in a subject wherein the case screw has markings to enable setting the case screw to a desired position.

In additional embodiments, a method for assessing reflexes in a subject wherein the subject is any of hypo-reflexive, normo-reflexive, or hyper-reflexive.

In additional embodiments, a method for assessing reflexes in a subject wherein the activation of the reflex testing apparatus elicits a deep tendon reflex that can be consistently repeated using the reflex testing apparatus in which the case screw is set to the same position.

BRIEF DESCRIPTION OF THE DRAWINGS

For a fuller understanding of the invention, reference should be made to the following detailed description, taken in connection with the accompanying drawings, in which:

FIG. 5A depicts the reflex testing device in a resting position. FIG. 5B depicts the reflex testing device under compression. FIG. 5C depicts the reflex testing device in a position after release.

FIG. 6A depicts the reflex testing device in a resting position. FIG. 6B depicts the reflex testing device under compression and/or after release.

DETAILED DESCRIPTION

Figure 1:
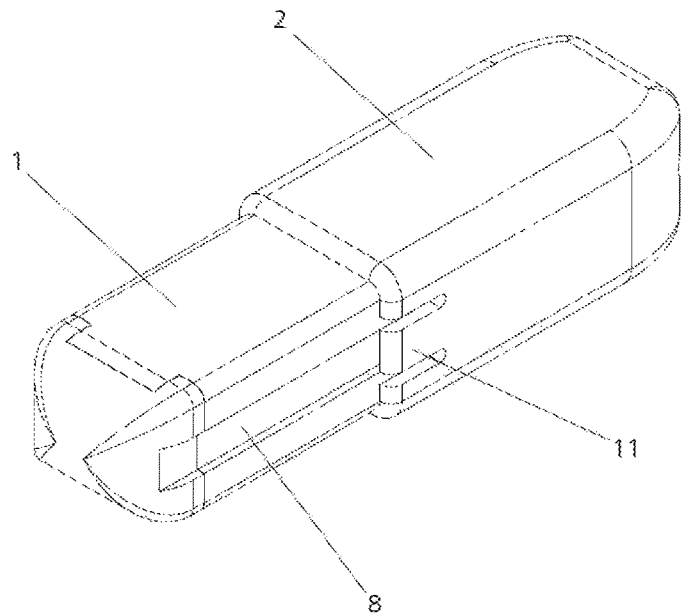
FIG. 1 is an isometric perspective view of a reflex testing device, according to an embodiment of the current invention.

In the following detailed description, reference is made to the accompanying drawings, which form a part thereof, and within which are shown by way of illustration specific embodiments by which the invention may be practiced. It is to be understood that other embodiments may be used, and structural changes may be made without departing from the scope of the present application. These embodiments are described in sufficient detail to enable those of ordinary skill in the art to practice the present disclosure, and it is to be understood that other embodiments may be utilized, and that structural, logical, and electrical changes may be made within the scope of the disclosure.

From the following descriptions, it should be understood that components of the embodiments as generally described and illustrated in the figures herein could be arranged and designed in a wide variety of different configurations. Thus, the following more detailed description of various embodiments, as represented in the figures, is not intended to limit the scope of the disclosure but is merely representative of various embodiments. While the various aspects of the embodiments are presented in drawings, the drawings are not necessarily drawn to scale unless specifically indicated.

The following description provides specific details, such as material types, compositions, material thicknesses, and processing conditions in order to provide a thorough description of embodiments of the disclosure. However, a person of ordinary skill in the art will understand that the embodiments of the disclosure may be practiced without employing these specific details. Indeed, the embodiments of the disclosure may be practiced in conjunction with conventional techniques employed in the industry. Only those process acts and structures necessary to understand the embodiments of the disclosure are described in detail below. A person of ordinary skill in the art will understand that some process components are inherently disclosed herein and that adding various conventional process components and acts would be in accord with the disclosure. In this description, specific implementations are shown and described only as examples and should not be construed as the only way to implement the present disclosure unless specified otherwise herein.

Illustrations presented herein are not meant to be actual views of any particular material, component, or system, but are merely idealized representations that are employed to describe embodiments of the disclosure. Referring in general to the following description and accompanying drawings, various embodiments of the present disclosure are illustrated to show its structure and method of operation. Common elements of the illustrated embodiments may be designated with similar reference numerals. It should be understood that the figures presented are not meant to be illustrative of actual views of any particular portion of the actual structure or method but are merely idealized representations employed to more clearly and fully depict the present invention defined by the claims below.

It should be understood that any reference to an element herein using a designation such as "first," "second," and so forth does not limit the quantity or order of those elements, unless such limitation is explicitly stated. Rather, these designations may be used herein as a convenient method of distinguishing between two or more elements or instances of an element. Thus, a reference to first and second elements does not mean that only two elements may be employed there or that the first element must precede the second element in some manner. Also, unless stated otherwise a set of elements may comprise one or more elements.

Any headings used herein should not be considered to limit the scope of embodiments of the invention as defined by the claims below and their legal equivalents. Concepts described in any specific heading are generally applicable in other sections throughout the entire specification.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

As used herein, "about" means approximately or nearly and in the context of a numerical value or range set forth means ±15% of the numerical. In an embodiment, the term "about" can include traditional rounding according to significant figures of the numerical value. In addition, the phrase "about 'x' to 'y'" includes "about 'x' to about 'y'".

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used in the specification and claims includes one or more such excipients, diluents, carriers, and adjuvants.

The term "therapeutically effective amount" as used herein describes concentrations or amounts of components such as agents which are effective for producing an intended result. Compositions according to the instant application may be used to effect a favorable change in the underlying condition, Whether that change is an improvement, relieving to some extent one or more of the symptoms of the condition being treated, and/or that amount that will prevent, to some extent, one or more of the symptoms of the condition that the host being treated has or is at risk of developing, or a complete cure of the disease or condition treated.

As used herein, the term "subject," "patient," or "organism" includes humans and mammals (e.g., mice, rats, pigs, cats, dogs, and horses). Typical hosts to which an agent(s) of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like.

The phrases "connected to" and "coupled to" refer to any form of interaction between two or more entities, including mechanical, electrical, magnetic, electromagnetic, fluid, and thermal interaction. Two components may be connected or coupled to each other even though they are not in direct contact with each other. For example, two components may be coupled to each other through an intermediate component.

The directional terms "proximal" and "distal" are used herein to refer to opposite locations on a medical device. The proximal end of the device is defined as the end of the device closest to the practitioner when the device is in use by the practitioner. The distal end is the end opposite the proximal end, along the longitudinal direction of the device, or the end furthest from the practitioner.

Figure 2:
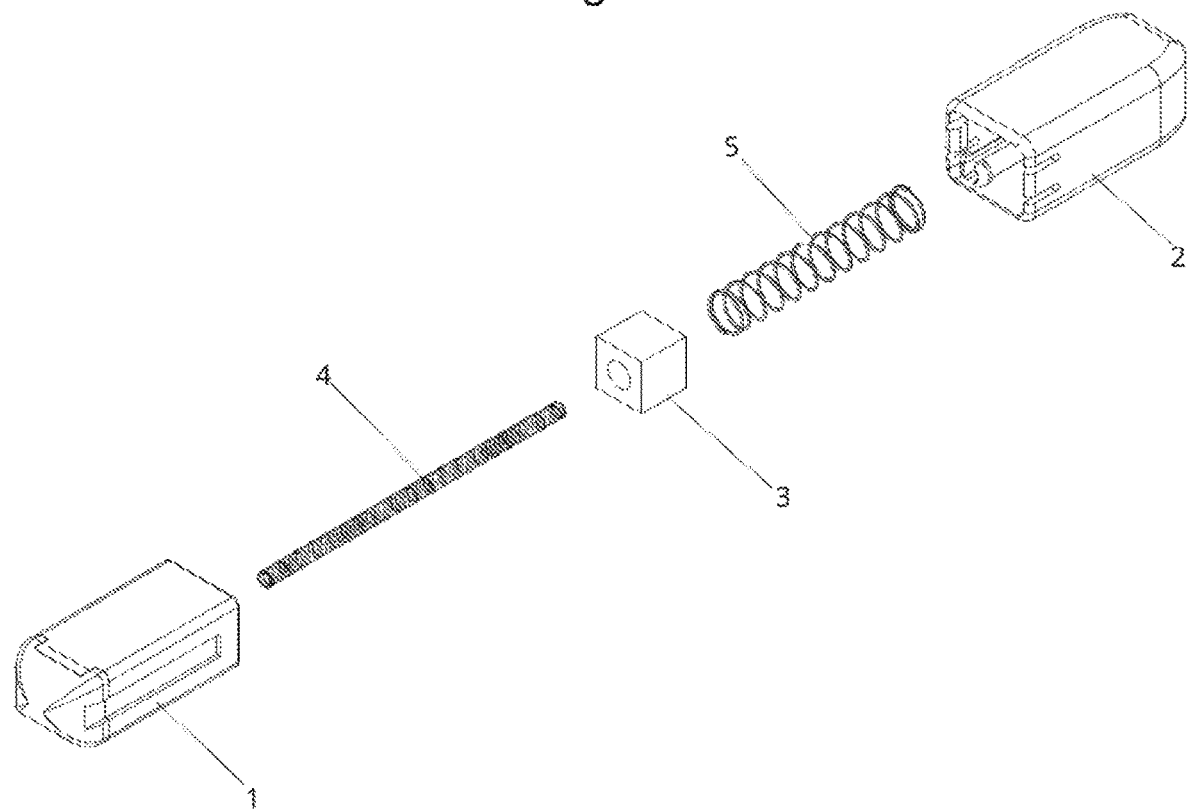
FIG. 2 is an exploded perspective view of the reflex testing device of FIG. 1.

Referring in general to the following description and accompanying drawings, various embodiments of the present disclosure are illustrated to show its structure and method of operation. Common elements of the illustrated embodiments may be designated with similar reference numerals. Accordingly, the relevant descriptions of such features apply equally to the features and related components among all the drawings. Any suitable combination of the features, and variations of the same, described with components illustrated in FIG. 1, can be employed with the components of FIG. 2, and vice versa. This pattern of disclosure applies equally to further embodiments depicted in subsequent figures and described hereinafter. It should be understood that the figures presented are not meant to be illustrative of actual views of any particular portion of the actual structure or method but are merely idealized representations employed to more clearly and fully depict the present invention defined by the claims below.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

Reflex testing apparatuses and methods are provided. The apparatuses can be used to elicit deep tendon reflex responses from patients (animals and/or humans). In some embodiments, a mechanism on the handheld apparatus can allow a user to adjust an impulse in which the apparatus produces, and a source of potential energy can be used to produce a desired impulse. The ability to control the impulse produced by the apparatus, or provided by the method, can provide the user with an ability to determine hypo-, normo-, or hyper-reflexic physiologic states of patients with an increased degree of consistency.

The use of a known mass impacting a tendon using some form of potential energy that gives the mass a velocity is provided. The end result, the impulse, can be pre-set and selected by the user, enabling him/her to quantify the DTR portion of the neurological assessment. This present disclosure is designed to enable the medical practitioner to objectively test DTRs by providing a consistent, measurable, and accurate impulse to a tendon.

In some embodiments, the apparatus can entail a mechanism, not limited to a mechanism that creates an impulse, to which an impulse is elicited. This impulse can be controlled by an external dial or adjustment mechanism that can provide the user with the ability to control the amount of impulse produced by the device. The impulse can be elicited onto a firm hammer or mallet that with the intent of the hammer or mallet to contact a living human or animal tendon. By contacting the tendon with a known amount of impulse, the user can then observe the reflex response consistently. Depending on the amount of reflex elicited, the user can know if the subject, human or otherwise, has hypo-, normo- or hyper-reflexic DTRs.

In some embodiments, an apparatus is provided apparatus for assessing reflexes of a patient's deep tendon, the apparatus comprising: an activatable hammer for contacting the patient's deep tendon when activated; a chamber for containing the activatable hammer; an impulse generator, in communication with the activatable hammer when inactive, for providing an impulse to the activatable hammer to activate the activatable hammer; a tuning mechanism, in communication with the impulse generator, for setting the impulse provided by the impulse generator to a predetermined strength; and an activation mechanism in communication with the impulse generator for releasing the impulse from the impulse generator thereby activating the hammer; wherein the reflexes of a patient's deep tendon are assessed by contacting the hammer to the patient's deep tendon and observing a reaction.

In some embodiments, a method of assessing the reflexes of a patient's deep tendon is provided, the method comprising: providing an automated reflex hammer, as described herein, having a hammer mass; activating the release of the hammer mass from the automated reflex hammer proximate the individual's deep tendon; allowing the hammer mass to contact the individual's tendon with a hammering impulse to initiate at least one reflex; observing the individual's deep tendon reflexes; whereby the individual's deep tendon reflexes are assessed.

The reflex testing apparatuses and methods provided can have multiple purposes, for example to decrease the inconsistency of the deep tendon reflex exam, to modify the kinematics of impulse delivery so as to reduce the physical space required to deliver the impulse allowing for accurate DTR assessments to be performed in spatially constrained areas, to quantify the impulse of the reflex test, and to provide for a means to best appreciate hypo-, normo-, and hyper- reflexive patients in the clinical setting.

Deep tendon reflexes (here simply referred to as reflexes) are muscle contractions which occur in response to stretching within muscles. These reflexes are normally present uniformly within all of a person's limbs. In neurology, reflexes are used to quickly determine the location of injury to the nervous system.

Reflexes are traditionally elicited by using reflex hammers. Reflex hammers are percussive devices used to strike at a tendon to induce sudden muscle stretching, which provokes a reflex response. Although many design variations of reflex hammer exist, the general principle of a hand-operated striking device is consistent among all of them. Reflex testing has the advantages of being fast, inexpensive, and noninvasive.

Reflexes are tested on both sides of the body at five major sites. In the arm, these include the biceps reflex, at the inside of the elbow; the brachioradialis, at the forearm; and the triceps, at the outside of the elbow. In the leg, these include the patellar reflex, at the kneecap; and the Achilles, at the back of the ankle. Test results are quantified subjectively on a scale of 0 to 4+, where 2+ is a normal reflex response.

Reflex testing can be limited under certain circumstances when a strike upon the tendon is obstructed. For example, an adequate reflex hammer swing may be impeded if a patient has a condition, such as contractures, which limit a patient's range of motion to a tense, closed position, giving insufficient room to swing a reflex hammer, particularly to test the biceps reflex. An adequate reflex hammer strike may also be impeded in cases of severe obesity, where parts of the patient's upper arm may physically block a reflex hammer from contacting the tendon site.

Quantifiable testing for reflexes is also limited, as striking with a hand-operated hammer results in a different amount of force transmission with each strike. Additionally, the subjective scaling system for reflexes is based mainly on an examiner's experience, rather than quantifiable methods.

A few mechanical devices for reflexes have been proposed to quantify reflexes in a reproducible fashion. In U.S. Pat. No. 2,800,895 to Torricelli, a number of spring-loaded reflex "guns" are proposed. These proposed devices deliver a consistent amount of force with each blow. However, they are triggered manually, and may be subject to variations in pressure when placing the device over the tendon. Additionally, each of these reflex "guns" uses an exposed striking surface, which may be obstructed from an adequate tendon strike in the scenarios described above.

World Intellectual Property Organization patent 2017027954 to Synew Corp describes a spring-powered impulse generator with a mass traveling within a chamber before contacting tissue. The chamber may act as a shroud to prevent obstruction of the hammer mass by contracture. Synew Corp's design includes a manually-operated trigger, although the mechanism of trigger is not clearly defined. Their patent claims a tunable mechanism with adjustable spring tension but is still subject to variations in pressure when placing the device due to use of a manually-operated trigger. Synew's patent also claims various "activation mechanisms" to trigger the impulse generator, although the nature of these mechanisms and their relation to the impulse generator is not clearly defined.

U.S. patents to Sweet, Spalding, and Adell and Starrett describe devices that release spring-loaded weights that drive weights forward. All of these devices are actuated by pressure upon a target surface. However, each of these devices uses a mechanism with multiple force-bearing surfaces contacting the released weight as well as the body of the device. These designs generate significant friction in operation, which limits their effectiveness in medical examination.

The current invention is a device actuated by pressure against a patient's skin. The pressure releases a spring-loaded mass that delivers an impulse through a fully-enclosed housing to a tendon site on the patient. The impulse is intended to elicit a reflex from the patient. In certain embodiments, the device provides diagnostic advantages in conditions where a manual reflex hammer strike on a tendon is obstructed by a patient's limited range of motion or where the patient suffers from severe obesity.

In certain embodiments, the current device includes a forward casing, a rear casing in communication with the forward casing, a weight contained within the casings, and a mainspring in communication with the weight. The mainspring has a bias toward expansion. In the resting position, the forward casing and the rear casing are separated or otherwise in an expanded disposition relative to each other. The casings may then be compressed together such that one casing overlaps the other substantially, and in this compressed position, the mainspring is also loaded. Maintaining the weight and mainspring in this position can be accomplished using any known mechanism. For example, the forward casing may contain a sear that holds the weight towards the end of the rear casing in preparation for release. When the sear is triggered by a ramp, the weight is released to be driven forward by the mainspring. The weight strikes the inside of the forward casing, delivering an impulse to a surface (e.g., skin) against which the device is pressed. To reset the device to its resting position, a reset spring can push apart the forward and rear casings. The weight can then be pulled back to its initial position by reset tabs attached to the rear casing.

EXAMPLE-STRUCTURE

In an embodiment, as depicted in FIGS. 1-4, the current invention is a reflex testing device. The exterior of the device, which can be seen in FIG. 1, includes forward casing 1 and rear casing 2. Casings 1 and 2 are held together or otherwise coupled together via assembly tab 11, which slides within assembly channel 8. The interior of the device, which can be seen in FIG. 2, includes piston or weight 3. Weight 3 is enclosed within the casings 1 and 2 and slides within the interiors of casings 1 and 2 under the force of mainspring 5. Reset spring 4 is biased toward pushing apart (i.e., expanding) casings 1 and 2 and impinges upon forward and rear casings 1 and 2, respectively. Mainspring 5 impinges upon weight 3 and rear casing 2.

Figure 3:
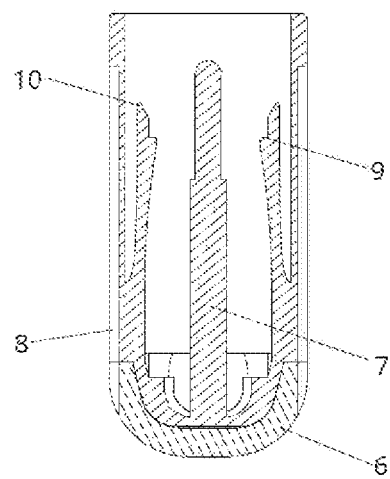
FIG. 3 is an elevated cross-sectional view of a forward casing of the reflex testing device of FIG. 1.

FIG. 3 depicts a cross section of forward casing 1. An elastomer head 6 is secured at the front end of the forward casing 1. The elastomer head 6 may be composed of elastomers such as silicone or urethane rubber. A reset spring support 7 extends from the front end of the forward casing 1 towards the rear. Assembly channels 8 are present on the sides of the forward casing 1. The forward casing 1 contains sear 9 and wedge 10, which are affixed to one another. The sear 9 includes a support surface, which faces away from the elastomer head 6, and an inside surface, which faces towards the reset spring support. In this embodiment, the sear 9 and wedge 10 are integrated into the casing as part of a flexible structure. A hinge mechanism may also attach the sear and wedge to the forward casing 1. In this embodiment, assembly channels 8, sear 9, and wedge 10 are symmetrically present on both sides of the forward casing 1.

Figure 4:
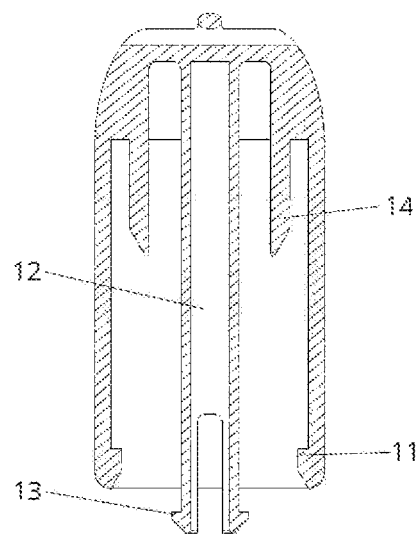
FIG. 4 is an elevated cross-sectional view of a rear casing of the reflex testing device of FIG. 1.

FIG. 4 depicts a cross section of rear casing 2. Assembly tab 11 is integrated into the casing as part of its structure. Reset tab 13 is attached to the casing by spring guide 12, which forms a hollow tube shape. Ramp 14 is rigidly attached to the rear of the casing. In this embodiment, assembly tabs 11, reset tabs 13, and ramp 14 are symmetrically present on both sides of the rear casing 2.

EXAMPLE-OPERATION

Figure 5A:
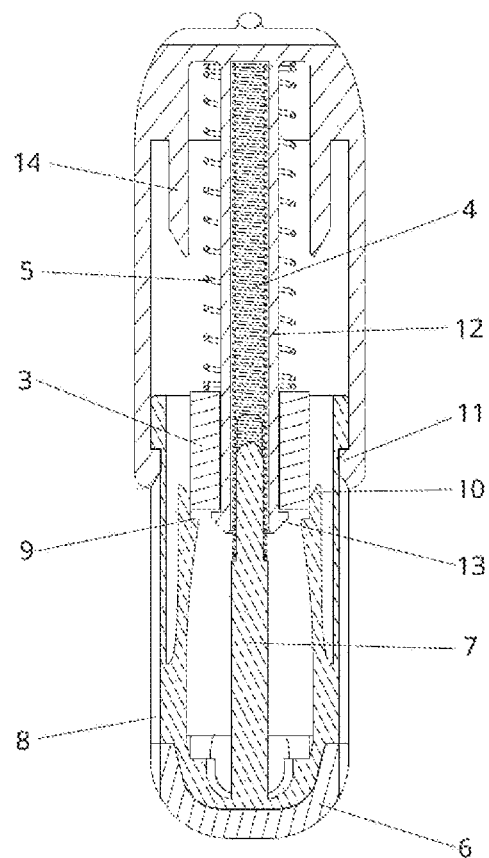
FIGS. 5A, 5B, and 5C are elevated cross-sectional views of a reflex testing device in various stages of use, according to an embodiment of the current invention.

Reflexes are elicited using the device by pressing the elastomer head 6 against the patient's skin over a tendon/target site. Operation begins with the device in a resting position depicted in FIG. 5A, where reset spring 4 and mainspring 5 are in extended positions. When pressed against the patient's skin, the forward casing 1 is pushed backwards into the rear casing 2. The sear 9, attached to the forward casing 1, pushes upon the weight 3, compressing the mainspring 5 against the back of the rear casing 2. Reset spring support 7, also attached to the forward casing, compresses reset spring 4 into spring guide 12.

Figure 5B:
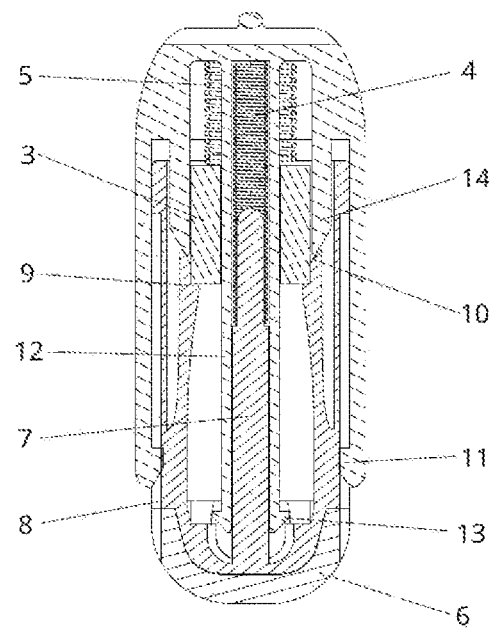

The fully compressed state of the device is depicted in FIG. 5B, where reset spring 4 and mainspring 5 are in compressed positions. Continued pressure against the patient's skin pushes wedge 10 against ramp 14. The ramp 14 pries the wedge 10 and sear 9 outwards from weight 3. When pried outwards completely, the sear 9 releases the weight 3, which travels forward under spring power from mainspring 5 to strike the front of the forward casing 1. Momentum from the weight 3 travels through the forward casing 1 and elastomer head 6, such that a force is placed upon the patient's tendon, thus inducing a reflex from the patient.

Figure 5C:
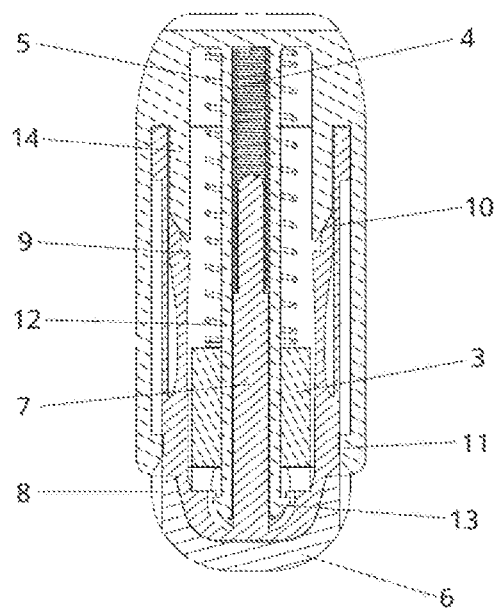

The released state of the device is depicted in FIG. 5C, where the reset spring 4 is in a compressed position and the mainspring 5 is in an expanded position. When the device is then withdrawn from the patient's skin, reset spring 4 pushes rear casing 2 backwards away from forward casing 1. Reset tab 13, attached to the rear casing by spring guide 12, is pulled backwards until it engages with weight 3. The weight 3 is dragged along the inner surface of sear 9 until it reaches the support surface, making it ready to be used again. The rear casing 2 is retained with the forward casing 1 by assembly tab 11, which stops against the end of the assembly channel 8.

Figure 6A:
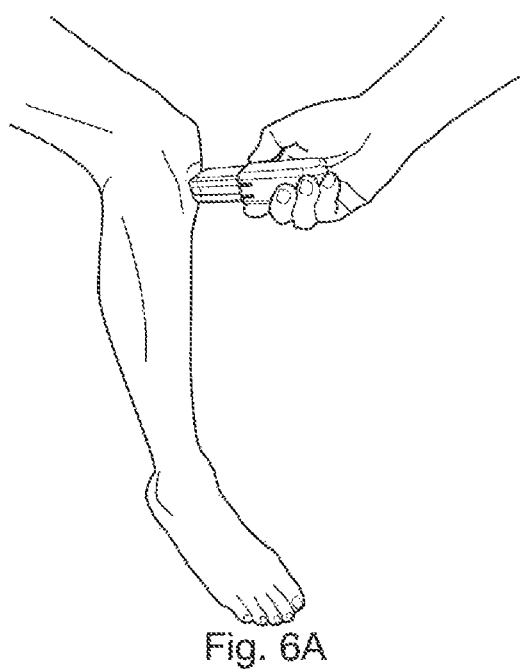
FIGS. 6A and 6B depicts use of a reflex testing device against a patient's knee, according to an embodiment of the current invention.
Figure 6B:
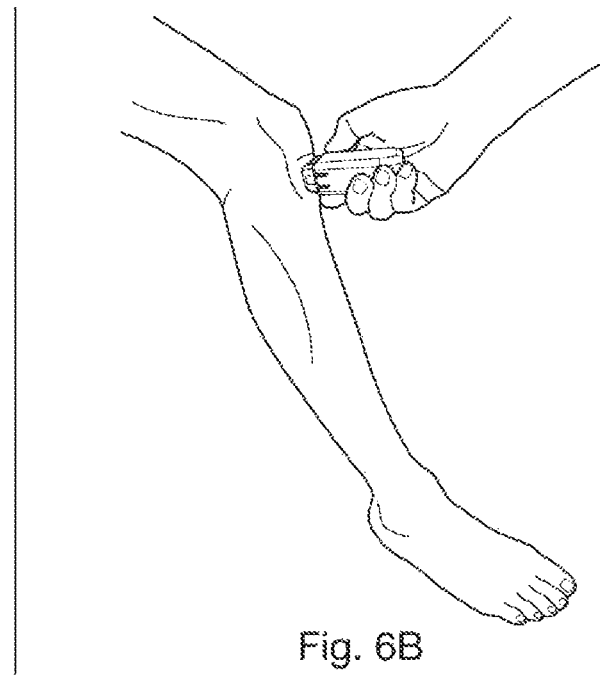

The use of the device is depicted in FIGS. 6A-6B. In FIG. 6A, the device is pressed against a patient's skin, and compressed until the weight is released, FIG. 6B depicts the device in the released state, after it has elicited a reflex. It can be understood that with the foregoing structure, the reflex testing device is capable of easily transferring stored momentum (i.e., stored within the mainspring 5) to the patient's tendon.

Figure 7A:
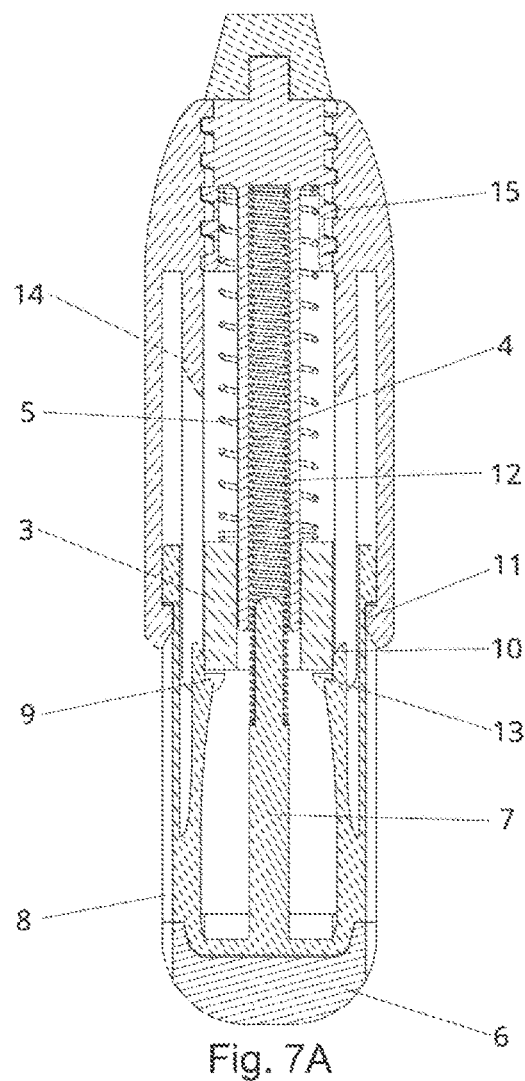
FIGS. 7A and 7B depict an embodiment with an adjustable variant of the device.
Figure 7B:
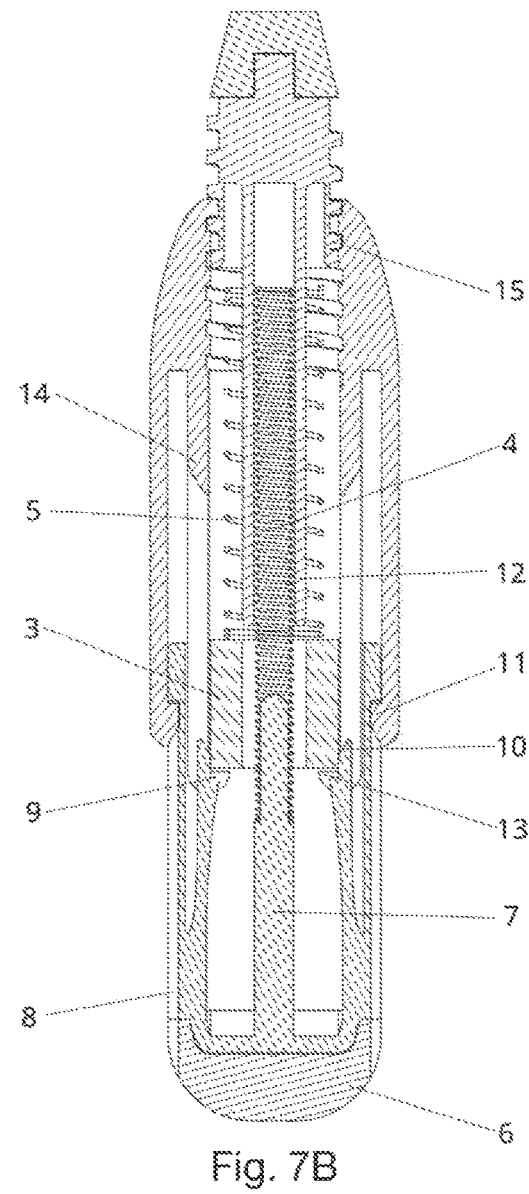

FIGS. 7A and 7B depict one possible adjustable variant of the device, which provides variable strike force. An adjustable tensioning device, in this case screw 15 is added, which allows variable tension to be placed on mainspring 5. Stops may be positioned at the ends of screw threads to prevent the screw from backing out of either side of the rear casing 2. FIG. 7A shows the device with the screw 15 in the fully forward position. FIG. 7B shows the device with the screw 15 in a rearward position, which relieves tension on mainspring 5 and reduces strike force. The case screw 15 has markings so an end user is able to set the case screw 15 to the same position desired with increased accuracy.

As described above, the embodiment depicted in FIG. 7A and 7B has a reset spring 4, mainspring 5 which impinges on weight 3. The device has an elastomer head 6. The device has a reset spring support 7, The device also has assembly channels 8, sear 9, and wedge 10. The device further has an assembly tab 11, reset tab 13 attached to the casing by spring guide 12, which forms a hollow tube shape. Ramp 14 is rigidly attached to the rear of the casing.

The advantages set forth above, and those made apparent from the foregoing description, are efficiently attained. While the disclosure is susceptible to various modifications and implementation in alternative forms, specific embodiments have been shown by way of non-limiting example in the drawings and have been described in detail herein. Since certain changes may be made in the above construction without departing from the scope of the instant application, it is intended that all matters contained in the foregoing description or shown in the accompanying drawings shall be interpreted as illustrative and not in a limiting sense.

The disclosure is not intended to be limited to the particular forms disclosed. Rather, the disclosure is to cover all modifications, equivalents, and alternatives falling within the scope of the disclosure as defined by the following appended claims and their legal equivalents.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art, and having the benefit of this disclosure, that changes may be made to the details of the above-described embodiments without departing from the underlying principles of the disclosure herein.

It is also to be understood that the following claims are intended to cover all of the generic and specific features of the invention herein described, and all statements of the scope of the invention that, as a matter of language, might be said to fall therebetween.

What is claimed is:

1. A device for assessing reflexes in a subject, comprising:
   a forward casing;
   a rear casing coupled to the forward casing;
   wherein the forward and the rear casing form a housing;
   the forward casing configured for moving from a first ready position to a second activated position;
   an impulse generator operably connected to the activatable hammer, where the impulse generator includes a weight which slides within the housing under the force of a mainspring, to provide an impulse to the forward casing causing the forward casing to move to the second activated position;
   a reset spring operably connected to the forward casing, wherein the reset spring facilitates return of the forward casing to the first ready position;
   a case screw operably connected to the impulse generator to provide control of the amount of force exerted by the impulse generator against the forward casing;
   wherein activation of the impulse generator causes the forward casing to exert force against the skin of the subject to elicit a reflex.

2. The device of claim 1, wherein the case screw comprises a stop at one end of the case screw to prevent the case screw from disengaging from the impulse generator, and where the case screw can be positioned by an end user to adjust the force exerted by the impulse generator against the forward casing.

3. The device of claim 1, wherein a stop is positioned to prevent the case screw from backing out of either side of the rear casing.

4. The device of claim 1, wherein the forward casing contains a sear that holds a weight toward an end of the rear casing in preparation for activation of the weight.

5. The device of claim 4, wherein when the sear is triggered by a ramp, the weight is released to be driven forward by the mainspring, the weight strikes an inside of the forward casing delivering an impulse to a surface against which the forward casing is pressed.

6. The device of claim 1, wherein the forward casing is coupled to the rear casing with an assembly tab which slides within an assembly channel.

7. The device of claim 1, further comprising an elastomer head secured at a front end of the forward casing.

8. The device of claim 7, wherein the elastomer head may be composed of elastomers selected from the group consisting of silicone and urethane rubber.

9. The device of claim 1, wherein the rear casing further comprises a ramp, an assembly tab, and a reset tab coupled to the rear casing by a spring guide which forms a hollow tube shape.

10. The device of claim 9, wherein the assembly tab, reset tab, and the ramp are symmetrically present on both sides of the rear casing.

11. The device of claim 1, wherein the case screw has exterior markings to allow for setting the case screw at the same position with increased accuracy.

12. A device for eliciting a deep tendon reflex in a subject, comprising:
a forward casing;
a rear casing coupled to the forward casing,
wherein the forward and rear casings collectively are a housing;
a weight enclosed within the housing;
a mainspring having one end positioned at a rear surface of the rear casing and the opposite end positioned on the weight, where the mainspring has a bias of expansion; and
a reset spring disposed through the weight and in communication with the rear casing and the front casing,
wherein the device includes a resting position, a compressed position, and a released position,
wherein the forward and rear casings are in slidable communication with each other between the expanded and compressed positions,
wherein in the expanded position, the mainspring is unloaded, and the reset spring is unloaded,
wherein in the compressed position, the mainspring is loaded, and the reset spring is loaded,
wherein in the released position, the mainspring is unloaded, and the reset spring is loaded, such that during a transition between the compressed position and the released position, the weight travels forward within the housing and places a force on a front surface of the forward casing.

13. A method of eliciting deep tendon reflex response from a subject, comprising:
providing a reflex testing apparatus;
wherein the reflex testing apparatus includes:
a forward casing;
a rear casing coupled to the forward casing;
wherein the forward and the rear casing form a housing;
wherein the forward casing is capable of moving from a first ready position to a second activated position;
an impulse generator operably connected to the forward casing, where the impulse generator provides an impulse to the forward casing to activate the forward casing to the second activated position;
a reset spring operably connected to the forward casing, wherein the reset spring facilitates return of the forward casing to the first ready position;
a case screw operably connected to the impulse generator to provide control of the amount of force exerted by the impulse generator against the forward casing;
positioning the reflex testing apparatus against the subject's skin over a tendon;
activating the reflex testing apparatus;
wherein activation of the reflex testing apparatus elicits a deep tendon reflex in the subject.

14. The method of claim 13, wherein the case screw has markings to enable setting the case screw to a desired position.

15. The method of claim 14, wherein the subject is any of hypo-reflexive, normo-reflexive, or hyper-reflexive.

16. The method of claim 15, wherein the activation of the reflex testing apparatus elicits a deep tendon reflex that can be consistently repeated using the reflex testing apparatus in which the case screw is set to the same position.

* * * * *